(12) United States Patent
Yabugami (10) Patent No.: US 9,125,619 B2
(45) Date of Patent: Sep. 8, 2015

(54) RADIOGRAPHIC EXAMINATION APPARATUS AND METHOD FOR THE SAME

(71) Applicant: SHIMADZU CORPORATION, Kyoto-Shi, Kyoto (JP)

(72) Inventor: Katsuhiro Yabugami, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 259 days.

(21) Appl. No.: 13/788,942

(22) Filed: Mar. 7, 2013

(65) Prior Publication Data

US 2014/0254751 A1 Sep. 11, 2014

(51) Int. Cl.
*A61B 6/00* (2006.01)
*H05G 1/34* (2006.01)
*H05G 1/22* (2006.01)

(52) U.S. Cl.
CPC .................. *A61B 6/485* (2013.01); *A61B 6/405* (2013.01); *A61B 6/487* (2013.01); *A61B 6/542* (2013.01); *H05G 1/34* (2013.01); *H05G 1/22* (2013.01)

(58) Field of Classification Search
CPC ........ A61B 6/485; A61B 6/405; A61B 6/487; A61B 6/542; H05G 1/10; H05G 1/22; H05G 1/34; H05G 1/30; H05G 1/32; H05G 1/56
See application file for complete search history.

(56) References Cited

U.S. PATENT DOCUMENTS 3,983,396 A * 9/1976 Mulleneers .................... 378/109
2013/0315378 A1* 11/2013 Yabugami ....................... 378/98

FOREIGN PATENT DOCUMENTS

JP 2004-139790 5/2004
JP 61-259498 5/2006
JP 2006-120548 5/2006

OTHER PUBLICATIONS

Pat. Appln. No. JP2010257404, Notification of Reasons for Refusal, dated Jun. 27, 2014, 2 pages—Japanese; 2 pages—English.

* cited by examiner

*Primary Examiner* — Glen Kao
(74) *Attorney, Agent, or Firm* — Andrew F. Young, Esq.; Lackenbach Siegel, LLP (57) ABSTRACT

A radiographic examination apparatus improves response to fluoroscopy or continuous shooting by changing promptly the power-output of an X-ray tube. The apparatus and method, when an absolute value of variation C per fixed time interval between the filament electric current of current pulse-output calculated by the filament electric current variation calculation element is more than a setup value, a flash control between pulse conducts increases or decreases temporarily the filament electric current between pulses to become the filament electric current on flash control between pulses calculated by a filament electric current calculation element based on a radiation condition of a current pulse-output and the radiation condition of following pulse-output.

11 Claims, 8 Drawing Sheets

|       | 40kV | 60kV | 80kV | 100kV | 110kV | 125kV |
|-------|------|------|------|-------|-------|-------|
| 20mA  | 3.69 | 3.65 | 3.63 | 3.62  | 3.61  | 3.60  |
| 63mA  | 4.06 | 4.03 | 4.00 | 3.99  | 3.97  | 3.96  |
| 125mA | 4.31 | 4.28 | 4.24 | 4.22  | 4.21  | 4.20  |
| 200mA | 4.57 | 4.48 | 4.43 | 4.40  | 4.39  | 4.38  |
| 360mA | 4.90 | 4.80 | 4.71 | 4.67  | 4.65  | 4.64  |
| 400mA | 4.95 | 4.85 | 4.76 | 4.71  | 4.69  | 4.68  |

RADIOGRAPHIC EXAMINATION APPARATUS AND METHOD FOR THE SAME

CROSS REFERENCE TO RELATED APPLICATIONS

This application relates to JP Ser. No. 2010-257404, filed Nov. 18, 2010 and published as JP Pub. No. 2012-109127 on Jun. 7, 2012, the entire contents of which are incorporated herein fully by reference.

FIGURE SELECTED FOR PUBLICATION

Figure 1:
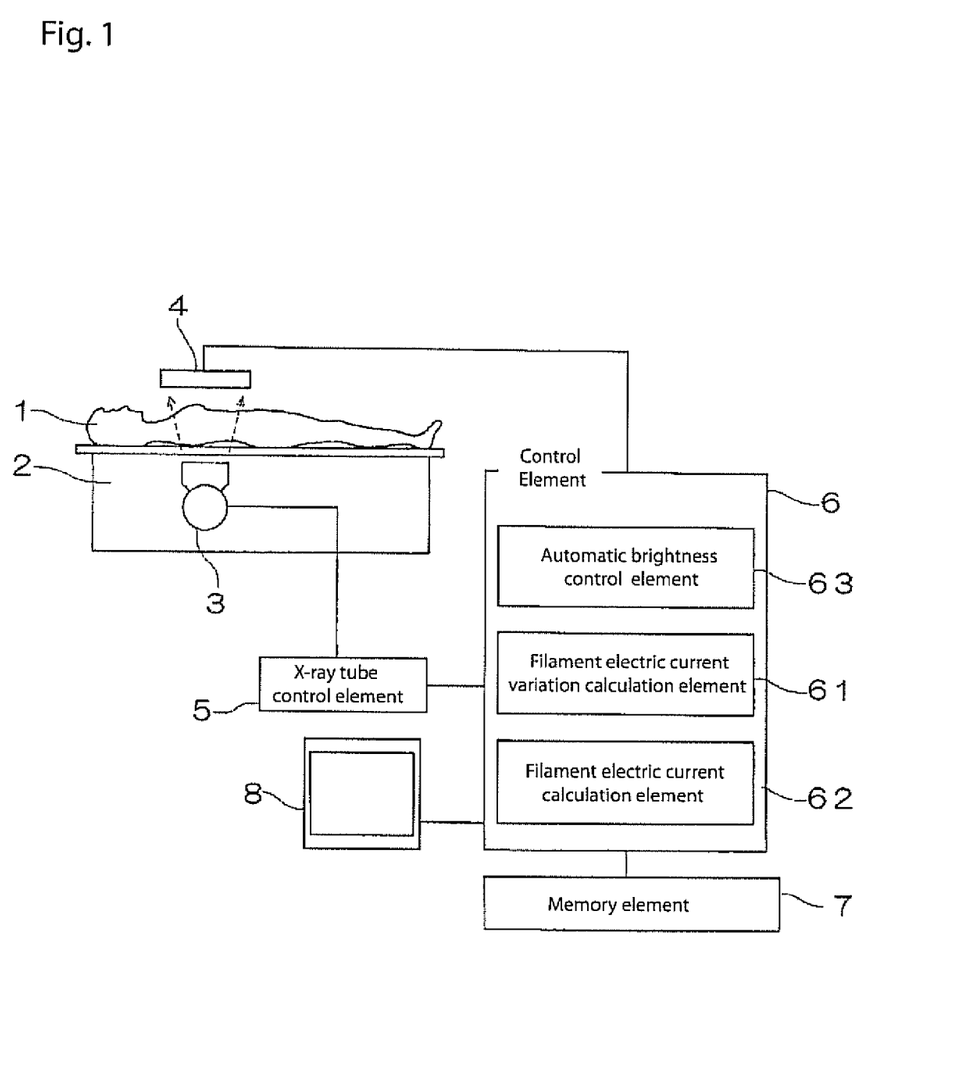
FIG. 1 is a schematic diagram illustrating a radiographic examination apparatus according to an embodiment of the present invention.

FIG. 1 is selected for publication

BACKGROUND OF THE INVENTION

1. Field of the Invention

The present invention relates to a radiographic examination apparatus to fluoroscope or to shoot continuously by using radiation and a method for the same.

2. Description of the Related Art

According to a conventional radiographic examination apparatus used for diagnosis or medical treatment, an X-ray image is detected along with an incident X-ray in an image intensifier (II) or a flat panel detector (FPD) after the x-ray irradiated from an X-ray tube passes through a subject. According to a radiographic examination apparatus to be used for an X-ray fluoroscopy, for example, the fluoroscopic image is obtained by a pulse output of approximately 7.5-60 fps (Frame per Second). Such radiographic examination apparatus comprises so-to-speak an automatic brightness adjustment mechanism to maintain consistent brightness by adjusting an amount of an incident X-ray by changing radiation conditions regardless subject's body size (deepness) or a part of subject's body. In addition, a radiographic examination apparatus to conduct continuous shooing approximately several frames to several 10 frames per second comprises a function to change an X-ray condition as to an X-ray pulse-output in accordance with subject's body size or a part of subject's body.

Such conventional X-ray conditions to be changed are three kinds of parameter, a tube voltage (kV), a tube electric current (mA) and a pulse width of fluoroscopy or shooting. Specifically, as radiation conditions should be changed in a broad range, for example, from an extremely low radiation dose condition on a fluoroscopy or continuous shooting through a hand (thin) to an extremely high radiation dose on examining the heart of a patient having thick (deep) chest from a diagonal direction, two parameters of tube voltage (kV) and tube electric current (mA) or three parameters including additionally a pulse width of fluoroscopy or shooting are controlled.

Then, the above parameter control is used also in order to automatically subject X-ray conditions to examination conditions, when not only an appropriate adjustment of such as brightness of image but also a continuous examination of subject's different parts by changing a relative position between an X-ray detector and a subject while fluoroscopy or continuous shooting is conducted.

Further, a control method for filament electric current, i.e. so-to-speak pre-flash, is suggested, by which the filament electric current is raised temporarily to promptly heat the filament of X-ray tube at the beginning of shooting. (Patent Document 1; JP Pub. 2006-120548).

PRIOR ART DOCUMENTS

Patent Document

Patent Document 1: JP Patent Published 2006-120548.

Accordingly, there is a need for an improved radiographic examination apparatus and method for the same that addresses one of the detriments noted herein.

ASPECTS AND SUMMARY OF THE INVENTION

In response, it is now recognized that there are several problems to be addressed.

Problems to be Solved by the Invention

According to the above conventional radiographic examination apparatus, when the target part is being switched from one part for which a low radiation dose fluoroscopy or continuous shooting can be applicable to the other part for which a high radiation dose is required under ongoing fluoroscopy or continuous shooting, some problems take place, in which the tube voltage becomes out of pre-set value or the tube electric current becomes too high.

Specifically, according to a general X-ray tube, a filament electric current value required to output a setup tube electric current corresponding to a setup tube voltage thereof is stored in a memory so that an output control of radiation can be conducted by changing the filament electric current with the setup tube electric current and a setup tube voltage. Then, the above described filament electric current is stored as a table of the relationship between the tube voltage and the tube electric current. However, if the filament temperature is lower than anticipated temperature despite the filament electric current controlled as a correct value, a smaller tube electric current than the expected tube electric current would be output because a factor in order to control the tube electric current is practically unmeasurable temperature of the filament. Further reversely, if temperature of the filament is higher than anticipated temperature despite the filament electric current controlled as a correct value, a larger tube electric current than the expected tube electric current would be output.

Also according to a conventional radiographic examination apparatus, when the target part is being switched from one part for which a low radiation dose fluoroscopy or continuous shooting can be applicable to the other part for which a high radiation dose is required under ongoing fluoroscopy or continuous shooting; or the target part is being switched from one part for which a high radiation dose fluoroscopy or continuous shooting is required to the other part for which a low radiation dose can be applicable under ongoing fluoroscopy or continuous shooting; it takes time wherein the filament temperature rises or downs to the required temperature, and accordingly, a problem takes place due to that a necessary response to follow mandatorily the transfer of shooting parts cannot be obtained. Such phenomena that occur not only when a target part is changed but also, e.g. when an initial radiation condition is far away from the target radiation condition are problems.

In addition, according to a radiographic examination apparatus also conducts a dual energy subtraction radiography to extract tissues having different radiation absorption coefficient by outputting alternatively the first pulse output on providing an X-ray tube with a high tube voltage and a low tube electric current and the second pulse output on providing the X-ray tube with a low tube voltage and a high tube electric current in a predetermined interval and by obtaining the subtraction image, a problem takes place due to that a necessary response to follow mandatorily the dual energy subtraction radiography because it also takes time that a temperature of the filament rises or downs to the required temperature between the first pulse-output and the second pulse-output.

Accordingly, as noted above, the present invention proposes to solve one or more of the above problems and another purpose of the present invention is to provide a radiographic examination apparatus that can follow efficiently fluoroscopy or continuous radiography by changing promptly the power output of an X-ray tube.

Means for Solving the Problem

According to one aspect of the present invention, there is provided a radiographic examination apparatus that not only pulse-outputs a radiation from an X-ray tube in predetermined time interval to conduct fluoroscopy and continuous radiography, but also changes the radiation condition of pulse-output by changing a filament electric current of X-ray tube; comprises a control element to conduct a flash control between pulses which temporarily increase or temporarily decrease a filament electric current between pulse-outputs based on the current radiation condition for pulse-output and the following radiation condition for pulse-output.

According to another aspect of the present invention, there is provided a control element comprising an filament electric current variation calculation element to calculate a variation C per unit time between a filament electric current of the current pulse-output and a filament electric current of the following pulse-output which are determined by a tube electric current and a tube voltage; and wherein the control element conducts a flash control when an absolute value of variation C per unit time between the filament electric current of the current pulse-output and the filament electric current of the following pulse-output calculated by the filament electric current variation calculation element is move than the setup value.

According to another aspect of the present invention, there is provided a filament electric current variation calculation element operative to obtain a tube voltage kV2 of the following pulse-output from a target image brightness Xr, a current image brightness X and a tube voltage kV1 of the current pulse-output, obtains a tube electric current I2 of the following pulse-output from the tube voltage kV2 and the data showing the relationship between a pre-stored tube voltage and the tube electric current, obtains a variation ΔI between the pulse-outputs of the filament electric current based on a tube electric current of the current pulse-output, a tube electric current of the following pulse-output, the a tube voltage kV1 of the current pulse-output and a tube voltage kV2 of the following pulse-output, and then a variation C per unit time between the filament electric current of the current pulse-output and a filament electric current of the following pulse-output is calculated by dividing the variation ΔI by the pulse-output interval Δt.

According to another aspect of the present invention, the control element comprises an filament electric current calculation element to calculate a filament electric current PI on the flash control between pulses, wherein filament electric current calculation element calculates a filament electric current PI according to the following formula on the flash control between pulses, in which G is a gain when the filament electric current varies, a tp is a flash time between pulse on the flash control between pulse and PI2 is a filament electric current on the following pulse-output.

$$PI = G \times C/tp + PI2$$

According to another aspect of the present invention, there is provided a radiographic examination apparatus for a dual energy subtraction radiography to obtain a subtraction image by alternatively outputting the first pulse-output when a low tube voltage and a high tube electric current are provided to an X-ray tube and the second pulse-output when a high tube voltage and a low tube electric current are provided to the X-ray tube in a predetermined interval comprises a control element to conduct a flash control between pulses by temporarily decreasing the filament electric current before the second pulse-output after the first pulse-output and also by temporarily increasing the filament electric current before the first pulse-output after the second pulse-output, based on the radiation condition on the first pulse-output and the radiation condition on the second pulse-output.

According to another aspect of the present invention, there is provided a control element comprising a filament electric current calculation element to calculate a variation C per unit time between the filament electric current on the first pulse-output and the filament electric current on the second pulse-output determined by a tube electric current and a tube voltage, wherein the control element conducts a flash control between the pulses when the variation C per unit time between the filament electric current on the first pulse-output and the filament electric current on the second pulse-output, which the filament electric current calculation element calculates therefore, is larger than the predetermined value.

Effects of the Invention

According to another aspect of the present invention, a power output of an X-ray tube can be promptly changed by controlling temperature of the filament by conducting a flash control between pulses, which temporarily increase or temporarily decrease the filament electric current between pulse-outputs, and accordingly a responsibility to follow fluoroscopy or continuous radiography can be improved thereby.

According to another aspect of the present invention, there is provided a means where power-output of the X-ray can be changed promptly by conducting a flash control between pulses and controlling temperature of the filament, when it is anticipated that a variation C per unit time between a filament electric current of the current pulse-output and a filament electric current of the following pulse-output would be more than a setup value and therefore a responsibility required to follow fluoroscopy and continuous radiography could not be obtained.

According to another aspect of the present invention, there is provided a radiographic examination apparatus wherein a variation C per unit time relative to the filament electric current can be easily calculated by utilizing a target image brightness Xr and a current image brightness X.

According to another aspect of the present invention, there is provided a radiographic examination apparatus wherein, a flash control between pulses can be accurately conducted by calculating a filament electric current PI on the flash control between pulses using the filament electric current calculation element.

According to another aspect of the present invention, there is provided a radiographic examination apparatus wherein a designated responsibility to follow the dual energy subtraction radiography can be improved by conducting the flash control between pulses, when the magnitude of X-ray tube filament electric current is switched alternatively to obtain a subtraction image.

According to another aspect of the present invention, there is provided a radiographic examination apparatus wherein a power-output of an X-ray tube can be changed promptly by controlling temperature of the filament by conducting a flash control between pulses, when it is anticipated that a variation C per unit time between the filament electric current on the first pulse-output and the filament electric current on the second pulse-output would be more than a setup value and a responsibility required to follow the dual energy subtraction radiography could not be obtained.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple', 'connect', 'join' and similar terms do not necessarily denote direct and immediate connections, but also include connections through intermediate elements or devices. It will be understood, that suitable operable processor, processor controls, programming, electronic elements, memory devices and suitable sensors as needed for the proposed invention and method will be understood by those of skill in the art as being included herein. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent or that steps may not be replaced or that intermediate steps may not be conducted within the scope of the invention.

The present invention is now illustrated below in various non-limiting embodiments. According to the present invention, an X-ray corresponds to a radiation of the present invention, but other forms of radiation may be used without departing from the invention.

Embodiments of the present invention are now illustrated referring to figures.

FIG. 1 is a schematic diagram illustrating a radiographic examination apparatus according to Embodiment 1 of the present invention, A radiographic examination apparatus comprise a table 2 to load a human 1 as a subject, an X-ray tube 3, a flat panel detector 4, an X-ray tube control element 5 to control a tube electric current and a tube voltage to be provided to the X-ray tube 3, a control element 6, a memory element 7 and a display element 8 such as a liquid crystal display panel or CRT. Further, the control element 6 comprises a filament electric current variation calculation element 61 and a filament electric current calculation element 62, and an automatic brightness control element 63 as described below.

A radiographic examination apparatus is to conduct fluoroscopy or continuous radiography, and comprises a structure to pulse-output an X-ray to a subject 1 on a table 2 from a X-ray tube 3, to detect the X-ray passed through the subject 1 by a flat panel detector 4, to conduct an image processing on X-rays detected by a control element 6, to display a fluoroscopic image or a continuous radiation shooting image using image-processed X-ray image signals on a display element 8, and to store the image information thereof in a memory element 7 when the continuous radiography occurs.

At this time, an automatic brightness control element 63 conducts a feedback control of a tube voltage and an electric current applied from the X-ray tube control element 5 to the X-ray tube 3 based on the signal from the flat panel detector 4 to keep constant brightness of an image displayed on the display element 8. For example, IBS circuit or ABC circuit is used as the automatic brightness control element 63.

Figure 2:
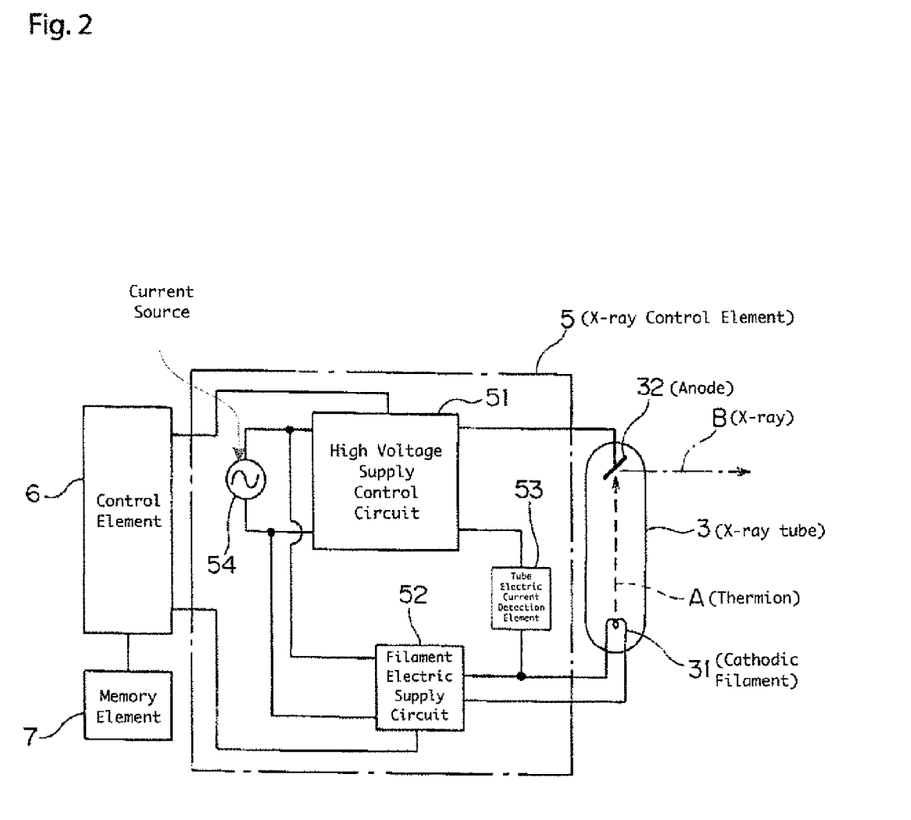
FIG. 2 is a block figure illustrating an X-ray tube control element, an X-ray tube, a control element and a memory element.

FIG. 2 is a block figure illustrating an X-ray tube control element 5, an X-ray tube 3, a control element 6 and a memory element 7.

The X-ray control element 5 comprises a high voltage supply circuit 51 and a filament electric current supply circuit 52 connected to a commercial alternating-current source 54. A high voltage supply control circuit 51 controls the tube voltage to be provided to the X-ray tube 3 by receiving the control signal from the control element 6. Further, a filament electric current supply circuit 52 controls the filament electric current to be supplied to a filament 31 of the X-ray tube 3 by receiving the control signal from the control element 6. A thermion A in the X-ray tube 3 emerges from the cathodic filament 31 which is provided with the filament electric current and is heated. The thermion A collides against an anode 32 which irradiates an X-ray B thereby. At this time, a tube electric current value when the X-ray tube 3 irradiates can be detected by a tube electric current detection element 53.

In addition, when the electric current value of the filament electric current to be supplied to the filament 31 increases, more thermion A would be emitted from the cathodic filament 31 to the anode 32, and accordingly more radiation dose would be irradiated because the tube electric current value becomes larger. Regardless, when temperature of the filament 31 is lower than anticipated temperature even if the same filament electric current is supplied a smaller tube electric current than the expected tube electric current would be output.

The above memory element 7 memorizes radiography conditions including the tube electric current and the tube voltage to be supplied to the X-ray tube on the radiation shooting and the filament electric current to be supplied to the filament 31 of the X-ray tube 3 under the radiography conditions thereof.

Figure 3:
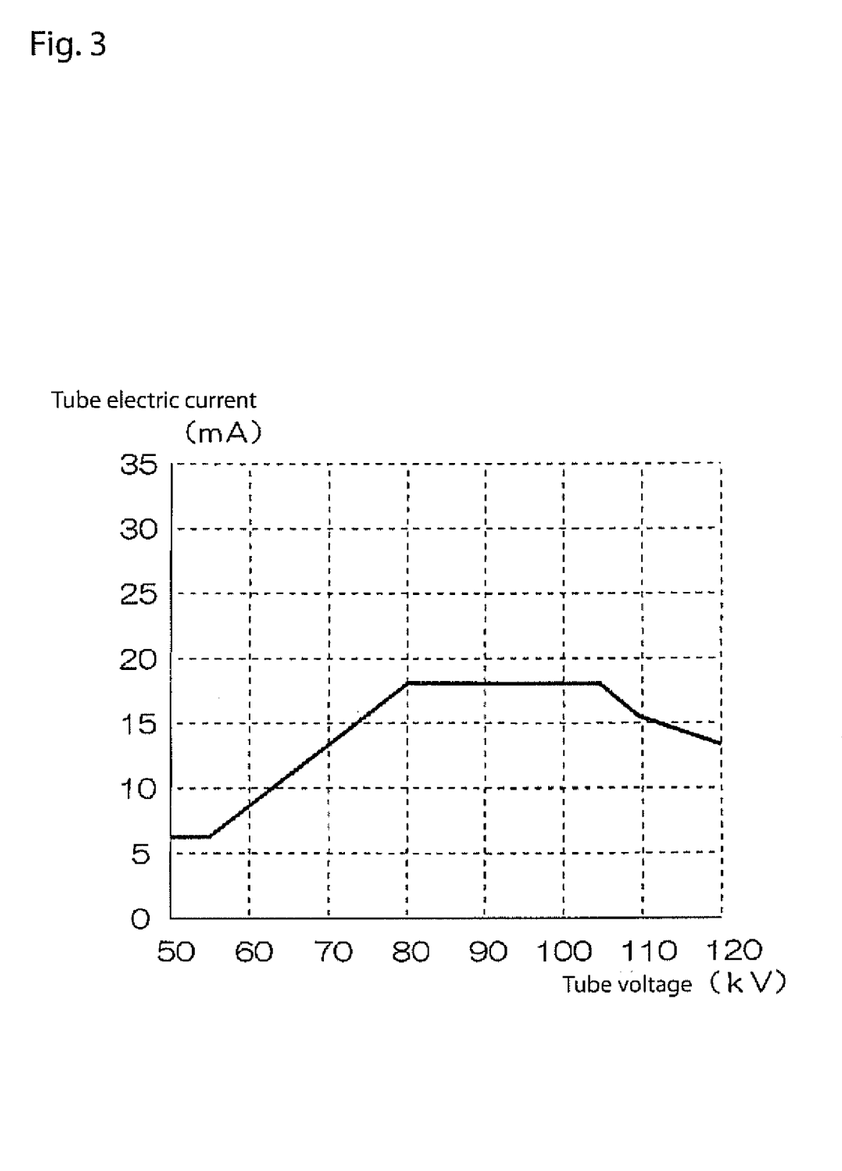
FIG. 3 is a graph illustrating a relationship between a tube electric current and a tube voltage to be supplied to an X-ray tube 3 on fluoroscopy.

FIG. 3 is a graph illustrating a relationship between a tube electric current and a tube voltage to be supplied to an X-ray tube 3 on fluoroscopy, which are stored in the memory 7.

Referring to FIG. 3, the thick-line curve shows the relationship between the tube voltage and the tube electric current to be supplied to the X-ray tube 3 on fluoroscopy. The tube voltage to be supplied to the X-ray tube 3 is adjusted to keep the brightness of the image displayed on the display element 8 constant on fluoroscopy. Then, once the tube voltage to be supplied to the X-ray tube 3 is determined, the tube electric current to be supplied to the X-ray tube 3 can be uniquely determined by the graph illustrated in FIG. 3.

Figure 4:
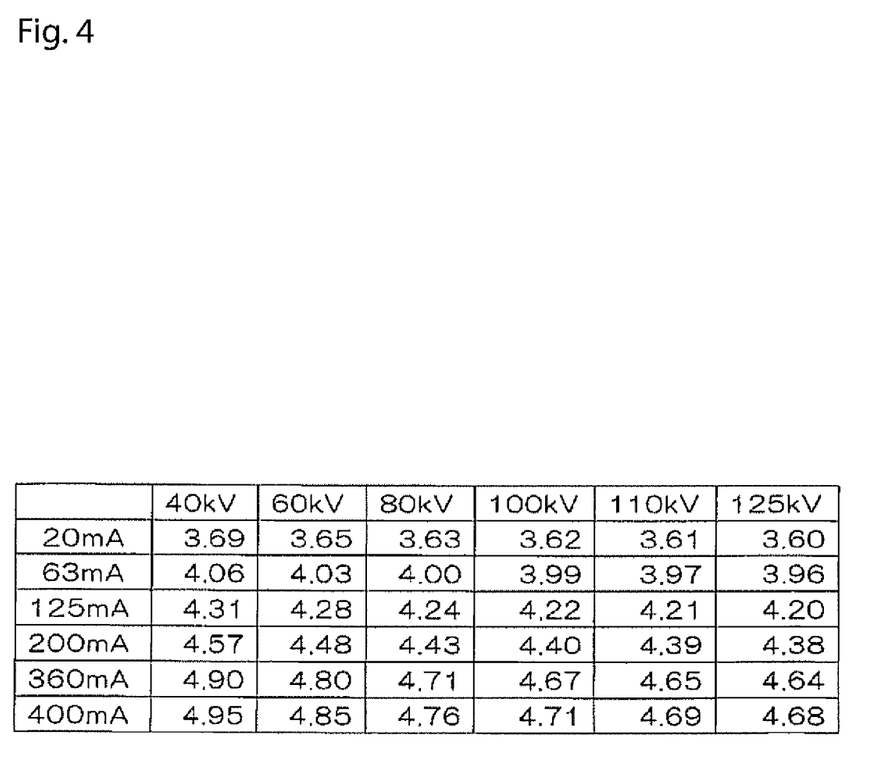
FIG. 4 is a table illustrating a relationship between a tube electric current and a tube voltage to be supplied to an X-ray tube 3 and a filament electric current thereon.

FIG. 4 is a table illustrating a relationship between a tube electric current and a tube voltage to be supplied to an X-ray tube 3 and a filament electric current thereon. By the way, the unit of the table is A (ampere).

Referring to FIG. 4, a filament electric current to conduct a radiographic radiography with predetermined tube voltage and tube electric current in the relationship with the tube voltage and the tube electric current to be supplied to the X-ray tube 3 is stored in the memory element 7 as a table. Further reversely, if temperature of the filament 31 is higher than anticipated temperature despite the filament electric current controlled as a correct value, a larger tube electric current than the expected tube electric current would be output. Specifically, the filament electric current I can be obtained as a function of a tube voltage kV and a tube electric current mA according to the formula (1) below.

$$I=f(kV,mA) \quad (1)$$

In addition, these filament electric current are obtained experimentally in advance. When any value not listed in the table as a tube voltage and as a tube electric current is adopted, a value interpolated using the table should be used.

Next, an operation is illustrated when fluoroscopy is conducted as a radiographic examination by using a radiographic examination apparatus according to Embodiment 1 above.

A tube voltage on the following pulse-output is determined from target image brightness Xr and current image brightness X when an X-ray is pulse-output in a predetermined interval. In this case, the below formula (2) can exist, wherein ΔkV is a tube voltage variation that is a difference between target image brightness Xr and current image brightness X and D is a parameter of response showing the relationship between image brightness and the tube voltage thereon.

$$\Delta kV=(Xr-X) \times D \quad (2)$$

In this case, the relationship between a tube voltage kV1 of current pulse-output and a tube voltage of the following pulse-output kV2 can be expressed as the formula (3) below.

$$kV2=kV1+\Delta kV \quad (3)$$

As shown in Formula (4) and Formula (5) below, a filament electric current I1 on the current pulse-output and the filament electric current I2 on the following pulse-output can be obtained as a function of a tube voltage kV1 and a tube electric current mA1 on current pulse-output and a tube voltage kV2 and a tube electric current mA2 on following pulse-output.

$$I1=f(KV1,mA1) \quad (4)$$

$$I2=(kV2,mA2) \quad (5)$$

Then, a variation Δ1 of the filament electric current between current pulse-output and following pulse-output is expressed as the formula (6) below.

$$\Delta 1=I2-I1 \quad (6)$$

According to Formula (7), a variation C of filament electric current per fixed time interval can be obtained by dividing a Δ1 of the filament electric current by an interval Δt of pulse-output. Now, the interval Δt of pulse-output is 33 ms if a frame rate of fluoroscopy is 30 fps (frame per second) and is 500 ms if it is 2 fps.

$$C=\Delta 1/\Delta t \quad (7)$$

The variation C of filament electric current per fixed time interval is calculated by a filament electric current variation calculation element 61 referring to FIG. 1.

Then, when the absolute value of variation C of filament electric current per fixed time interval is more than a setup value, a flash control between pulses to increase temporarily the filament electric current or to decrease temporarily between pulse-outputs is conducted.

In addition, when the frame rate of fluoroscopy is small and the pulse-output interval of X-ray is long despite relatively large variation of filament electric current, a responsibility to follow fluoroscopy can be obtained by controlling temperature of the filament 31. On the other hand, when the frame rate of fluoroscopy is large and the pulse-output interval of X-ray is short despite relatively small variation of filament electric current, it would be difficult to obtain a responsibility to follow fluoroscopy by controlling temperature of the filament 31. Therefore, a radiographic examination apparatus according to Embodiment of the present invention conducts a flash control between pulses when an absolute value of the variation C of filament electric current per fixed time interval is more than a setup value.

Figure 5A:
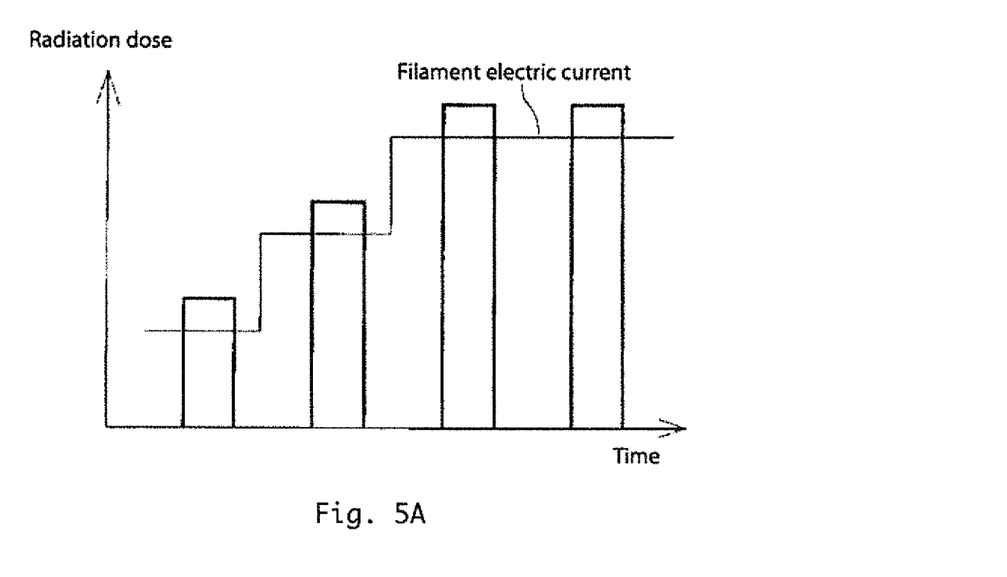
FIGS. 5A and 5B are explanation drawings illustrating a flash control between pulses.
Figure 5B:
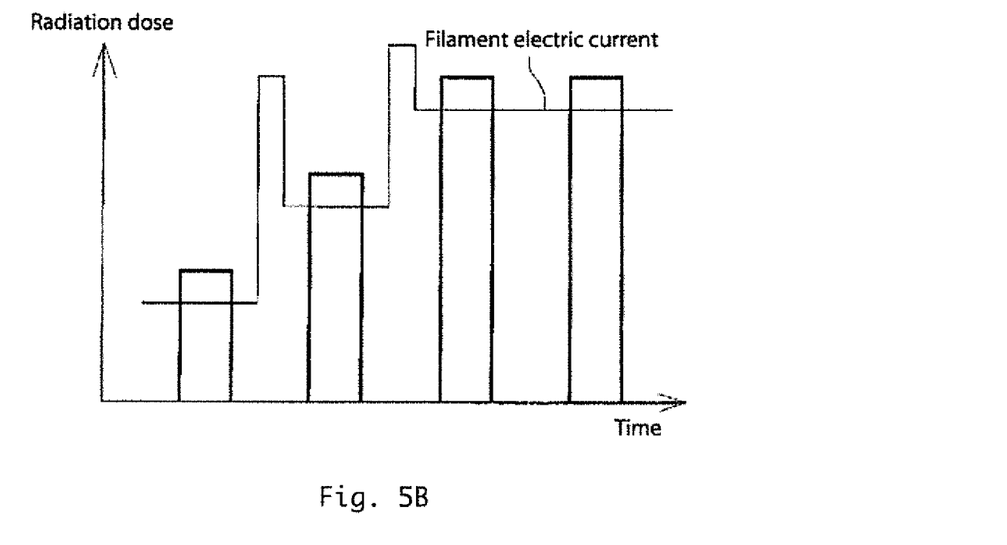
Figure 6A:
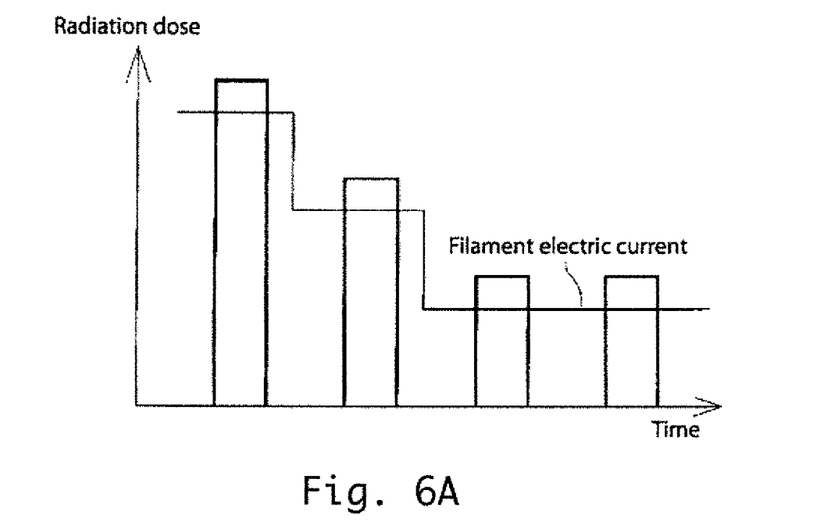
FIGS. 6A and 6B are explanation drawings illustrating a flash control between pulses.
Figure 6B:
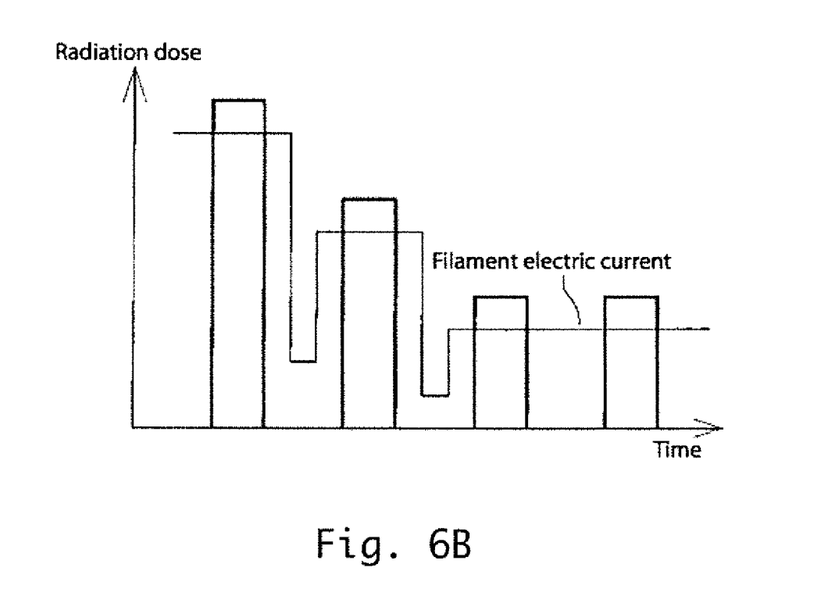

FIGS. 5A-5B and FIGS. 6A-6B are explanation drawings illustrating a flash control between pulses. Now, FIG. 5 illustrates the case in which a radiation dose is gradually increasing, and FIGS. 6A-6B illustrate the case in which a radiation dose is gradually decreasing.

The flash control between pulses is a control manner whereby a filament electric current between pulse-outputs is temporarily increased or temporarily decreased. Referring to FIG. 5, when the radiation dose gradually increases, further referring to FIG. 5A, the filament electric current conventionally is increased corresponding to the radiation dose (magnitude of tube electric current) on pulse-output of radiation. However, when the increase rate of radiation dose is high and the variation C of filament electric current per fixed time interval is more than a setup value, it takes time until temperature of the filament 31 rises to a required temperature and accordingly any necessary response to the change of radiation dose cannot be attained whereby it becomes problematic so that a necessary responsibility to follow such as transfer of a radiography part cannot be obtained. Accordingly, when the radiation dose gradually increases, referring to FIG. 5B, the filament electric current is temporarily increased between pulse-outputs so that temperature of the filament 31 can be risen quickly and the radiation dose can be increased promptly to improve the responsibility to follow the fluoroscopy.

Meanwhile, in the present description, a flash between pulses means an operation to change temporarily filament electric current relative to a flash control between pulses wherein filament electric current is temporarily increased or temporarily decreased between pulse-outputs. And then, in this case, Formula (8) below can exist, wherein tp is flash time between pulses (time to change temporarily filament electric current), PI is a flash electric current between pulses (a changed filament electric current), and PI2 is a filament electric current on the following pulse-output.

$$PI = Gu \times C/tp + PI2 \qquad (8)$$

Gu is, here, a gain when a filament electric current changes in an increase direction. Specifically, Gu is a coefficient to determine a flash electric current PI between pulses based on the above filament electric current variation C ($C = \Delta I/\Delta t$) and the flash time tp between pulses when temperature of the filament is risen.

On the other hand, referring to FIGS. 6A-6B, when the radiation dose increases gradually, the filament electric current conventionally, referring to FIG. 6A, has been decreased corresponding to the radiation dose (magnitude of tube electric current) on pulse-output of X-ray. However, when the decrease rate of radiation dose is high and the absolute value of variation C of filament electric current per fixed time interval is more than a setup value, it takes time until temperature of the filament 31 downs to a required temperature and accordingly any necessary response to the change of radiation dose cannot be attained whereby it becomes problematic so that a necessary responsibility to follow such as transfer of a radiography part cannot be obtained. Accordingly, when the radiation dose gradually decreases, referring to FIG. 6B, the filament electric current is temporarily decreased between pulse-outputs so that temperature of the filament 31 can be downed quickly and the radiation dose can be decreased promptly to improve the responsibility to follow fluoroscopy.

In this case, Formula (9) below can exist, if Gd is a coefficient to determine a flash electric current PI between pulses based on the above filament electric current variation C ($C = \Delta I/\Delta t$) and the flash time tp between pulses when the filament temperature is downed, wherein Gd is a gain when the filament electric current is changed in a decreasing direction.

$$PI = Gd \times C/tp + PI2 \qquad (9)$$

In addition, if the gain Gu when the filament electric current is changed in an increasing direction and the gain Gd when the filament electric current is changed in a decreasing direction are identical, either Formula (8) or Formula (9) can be used. The above flash electric current PI between pulses, here, can be calculated by an electric current calculation element 62 as shown in FIG. 1.

As described above, according to a radiographic examination apparatus according to Embodiment 1 of the present invention, a power output of an X-ray tube can be promptly changed by controlling temperature of the filament by conducting a flash control between pulses, which temporarily increases or temporarily decreases the filament electric current between pulse-outputs when an absolute value of variation C of filament electric current per fixed time interval is more than a setup value, and accordingly a responsibility to follow fluoroscopy and continuous radiography can be improved thereby.

Figure 7:
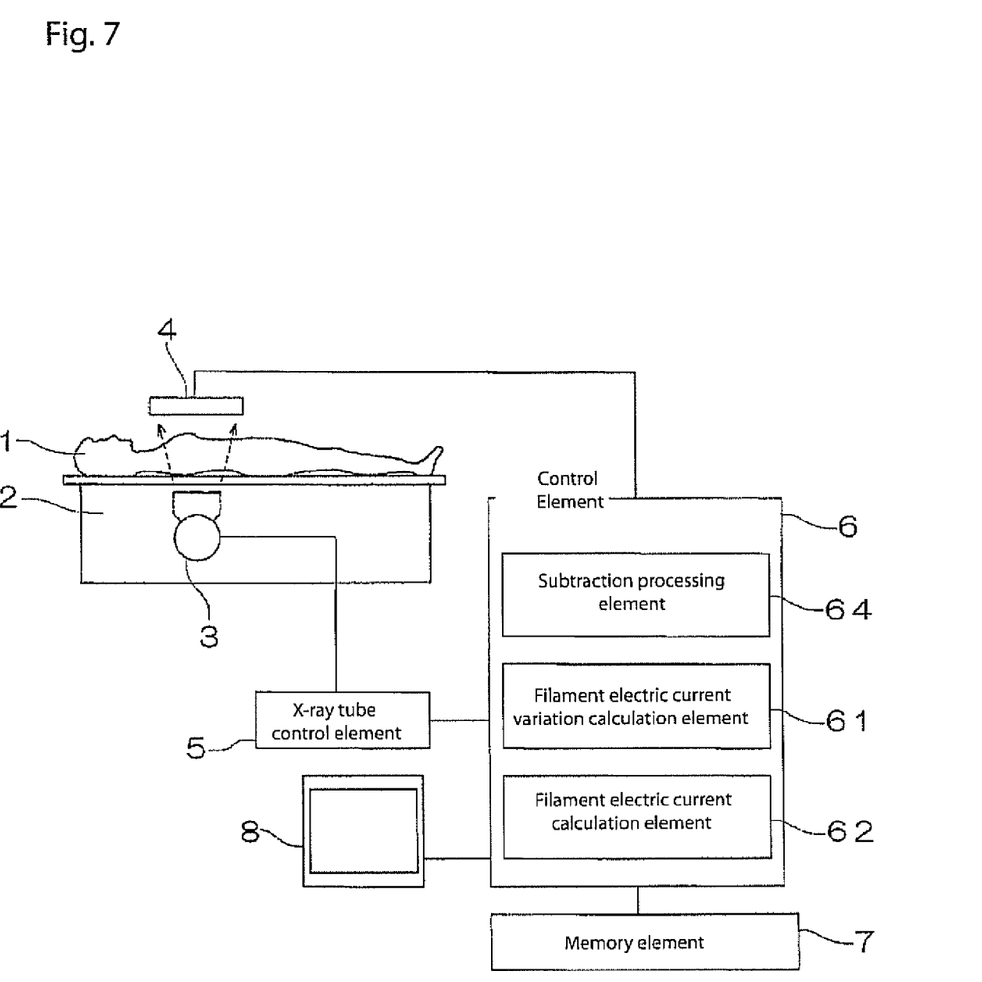
FIG. 7 is a schematic diagram illustrating a radiographic examination apparatus according to another embodiment of the present invention.

Next, the other Embodiment of the present invention is illustrated. FIG. 7 is a schematic diagram illustrating a radiographic examination apparatus according to Embodiment 2 of the present invention, Further, the same constitution as illustrated in Embodiment 1 is not described in detail while providing the identical reference letter.

A radiographic examination apparatus according to Embodiment 2, is for a dual energy subtraction radiography to obtain a subtraction image by alternatively outputting the first pulse-output when a low tube voltage and a high tube electric current are provided to an X-ray tube 3 and the second pulse-output when a high tube voltage and a low tube electric current are provided to an X-ray tube 3 in a predetermined interval for the purpose of extraction of tissues having a different radiation absorption coefficient. A control element 6 of the radiographic examination apparatus according to Embodiment 2 comprises a filament electric current variation calculation element 61, a filament electric current calculation element 62 and a subtraction processing element 64 to conduct a subtraction processing as well as Embodiment 1.

Figure 8A:
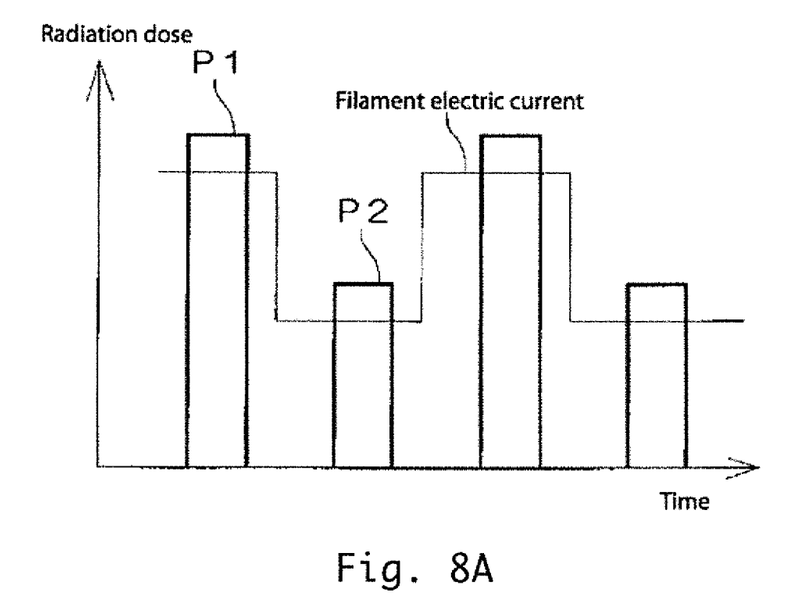
FIGS. 8A and 8B are explanation drawings illustrating a flash control between pulses according to a radiographic examination apparatus according to another embodiment.
Figure 8B:
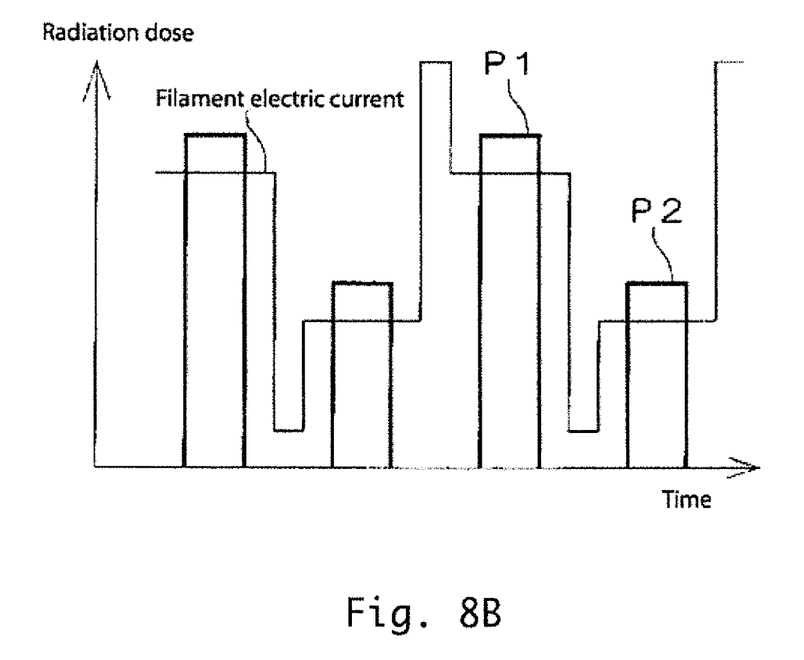

FIG. 8 is an explanation drawing illustration a flash control between pulses according to a radiographic examination apparatus according to Embodiment 2.

Referring to FIGS. 8A-8B, the first pulse-output P1 outputting an X-ray of high radiation dose by providing the X-ray tube 3 with a low tube voltage and a high tube electric current and the second pulse-output P2 outputting an X-ray of low radiation dose by providing the X-ray tube 3 with a high tube voltage and a low tube electric current are output alternatively in a predetermined interval to conduct the subtraction on the dual energy subtraction radiography. Referring to FIG. 8A, the filament electric current is conventionally increased or decreased corresponding to the radiation dose (magnitude of tube electric current) on pulse-output of X-ray.

However, when the decrease rate of radiation dose is high and the absolute value of variation C of filament electric current per fixed time interval is more than a setup value, it takes time until temperature of the filament 31 downs or rises to a required temperature, and accordingly any necessary response to the change of radiation dose cannot be attained whereby it becomes problematic so that a necessary responsibility to follow such as transfer of radiography parts cannot be obtained. Therefore, according to Embodiment 2, a flash control between pulses is conducted by temporarily decreasing the filament electric current before the second pulse-output P2 after the first pulse-output PI, and also by increasing the filament electric current before the first pulse-output P1 after the second pulse-output P2.

According to a radiographic examination apparatus of Embodiment 2, the flash control between pulses is conducted; when it is decided whether the flash control between pulses is necessary or not; and when the variation $\Delta 1$ of filament electric current is obtained according to the above Formula (6) from difference of filament electric current between the filament electric current on the first pulse-output p1 and the filament electric current on the second pulse-output, and also the variation C of filament electric current per fixed time interval is obtained according to the above Formula (7), and then the absolute value of variation C of filament electric current per fixed time interval is more than a setup value.

Then, according a radiographic examination apparatus of Embodiment 2, a flash electric current P1 between pulses is also calculated according to the above Formula (8) or Formula (9). Then, if an radiation condition for the first pulse-output P1 and the second pulse-output P2 is always constant, the calculation of flash electric current P1 between pulses might be conducted only once at the beginning.

According to a radiographic examination apparatus of Embodiment 2 of the present invention, a power output of an X-ray tube can be promptly changed by controlling the temperature of a filament according to changing alternatively a flash control between pulses, the filament electric current between pulse-outputs when an absolute value of variation C of filament electric current per fixed time interval is more than a setup value, and accordingly, a responsibility to follow the fluoroscopy and continuous radiography can be improved thereby.

EXPLANATION OF REFERENCES

1—Subject
2—Table
3—X-ray tube
4—Flat panel detector
5—X-ray tube control element
6—Control element
7—Memory element
8—Display element
31—Filament
32—Anode
51—High voltage supply circuit
52—Filament electric current supply circuit
61—Filament electric current variation calculation element
62—Filament electric current calculation element
63—Automatic brightness control element
64—Subtraction processing element It will be understood by those of skill in the art that the phrases radiography will be noted as descriptive of a process, method, or apparatus or system for taking images of opaque objects, typically with X-ray radiation (although not limited thereto). This process can be optionally described loosely as 'shooting' or instructing the radiography or shooting a radiograph or taking a radiograph. These shall be understood as descriptive within the field of art and understood by those skilled therein as being within the scope and spirit of the present invention.

It will be understood by those of skill in the art that the use of the phrases constitute, constitution, comprising, exemplary, embodiment, illustration, step, or system are provided as assistive aids to the reader and are not used to imply a required limiting arrangement or structure or assembly of features or aspects or functions or method steps to the invention. The aspects of the invention as discussed herein are to be considered broadly and without limitation. For example, the operative method steps may be modified for use during operation of the apparatus and systems proposed, such that multiple methods of operating the same may be readily accommodated without departing from the scope and spirit of the proposed invention. It will be further understood by those of skill in the art that the use of the phrase means may be interchangeably used with the phrase element, system, or feature, to be operably understood by those of suitable skill. Thus, that the feature, aspect, means, or element will be as described and function as enabled or described within the skill of one of the art.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure covers modifications and variation of this invention provided they come within the scope of the appended claims and their equivalents.

What is claimed is:

1. A radiographic examination apparatus, comprising:
   a control element operative to conduct a flash control between pulses to increase temporarily or decrease temporarily a filament electric current between pulse-outputs;
   said control element operating based on a radiation condition of a current pulse-output and a radiation condition of a following pulse-output;
   wherein the radiographic examination apparatus is operative to conduct a fluoroscopy and a continuous shooting by a pulse-outputting radiation from an X-ray tube in a predetermined interval, and
   wherein the radiographic examination apparatus also is operative to change the radiation condition of said pulse-outputting radiation by changing the filament electric current of said X-ray tube.

2. A radiographic examination apparatus, according to claim 1, wherein:
   said control element comprises:
      a filament electric current variation calculation element to calculate a variation C per fixed time interval between the current filament electric current and a following filament electric current, which are determined according to a tube electric current and a tube voltage, and
   said control element is operative to conduct said flash control between pulses, when a variation C per fixed time interval, between the filament electric current of the current pulse-output and the filament electric current of the following pulse-output, is respectively calculated by said filament electric current variation calculation element.

3. A radiographic examination apparatus, according to claim 2, wherein:
   said filament electric current variation calculation element obtains:
      a tube voltage kV2 of the following pulse-output from a target image brightness Xr, a current image brightness X and a tube voltage kV1 of the current pulse-output;
      a tube electric current I2 of the following pulse-output from data indicating the relationship between the tube voltage kV2 and a pre-memorized tube voltage and tube electric current;
      a variation ΔI between pulse-outputs of said filament electric current based on the present tube electric current I1 of the current pulse-output; the tube electric current I2 of the following pulse-output, the present tube voltage kV1, and the tube voltage kV2 of the following pulse-output, and
   calculates a variation C per fixed time interval, between said filament electric current of the current pulse-output and said filament electric current of the following pulse-output, by dividing the variation ΔI by the interval Δt of pulse-output.

4. A radiographic examination apparatus, according to claim 2, wherein:
   said control element further comprises:
      a filament electric current calculation element operative to calculate a filament electric current PI of said flash control between pulses; and
   whereby the filament electric current calculation element calculates the filament electric current PI of said flash control between pulses according to the following formula PI=G×C/tp+PI2, wherein a gain when changing the filament electric current is G, a flash time between pulses of the flash control between pulses is tp, and the filament electric current of the following pulse-output is PI2.

5. A radiographic examination apparatus, according to claim 3, wherein:
said control element further comprises:
a filament electric current calculation element operative to calculate a filament electric current PI of said flash control between pulses; and
whereby the filament electric current calculation element calculates the filament electric current PI of said flash control between pulses according to the following formula PI=G×C/tp+PI2, wherein a gain when changing the filament electric current is G, a flash time between pulses of the flash control between pulses is tp, and the filament electric current of the following pulse-output is PI2.

6. A radiographic examination apparatus, comprising:
a radiographic examination apparatus for dual energy subtraction shooting operative to obtain a subtraction image by outputting a first pulse-output provided with a low tube voltage and high tube electric current relative to an X-ray tube and a second pulse-output provided with a high tube voltage and low tube electric current relative to said X-ray tube alternatively in a predetermined interval;
said radiographic examination apparatus comprising:
a control element operative to conduct a flash control between said respective pulses by temporarily decreasing a filament electric current before the second pulse-output after the first pulse-output; and
said control element operative to increase the filament electric current before the first pulse-output after the second pulse-output based on a radiation condition of said first pulse-output and a radiation condition of said second pulse-output.

7. A radiographic examination apparatus, according to claim 6, wherein said control element further comprises:
a filament electric current variation calculation element operative to calculate a variation C per fixed time interval between the filament electric current of the first pulse-output and the filament electric current of the second pulse-output, which are determined according to a tube electric current and a tube voltage, and
wherein said control element is operative to conduct said flash control between pulses when the variation C per fixed time interval, between the filament electric current of the first pulse-output and the filament electric current of the second pulse-output calculated by the filament electric current variation calculation element is more than a setup value.

8. A method for operating a radiographic examination apparatus, comprising the steps of:
operating a control element to conduct a flash control between pulses;
said flash control being one of a temporary increase and a temporary decrease in a filament electric current between respective pulse-outputs;
determining a radiation condition of a current pulse-output and a radiation condition of a following pulse-output and conducting said step of operating said control element based upon the respective radiation conditions;
conducting a fluoroscopy and a continuous shooting by a pulse-outputting radiation from an X-ray tube in a predetermined interval; and
changing a radiation condition of said pulse-outputting radiation by changing the filament electric current of said X-ray tube.

9. A method of operating a radiographic examination apparatus, according to claim 8, further comprising the steps of:
calculating, with a filament electric current variation calculation element, a variation C per fixed time interval, between the current filament electric current and a following filament electric current, which are determined according to a tube electric current and a tube voltage; and
conducting, with said control element, said flash control between pulses, when a variation C per fixed time interval, between the filament electric current of the current pulse-output and the filament electric current of the following pulse-output, is calculated respectively by said filament electric current variation calculation element.

10. A method of operating a radiographic examination apparatus, according to claim 9, further comprising the steps of:
obtaining, by said filament electric current variation calculation element;
a tube voltage kV2 of the following pulse-output from a target image brightness Xr, a current image brightness X and a tube voltage kV1 of the current pulse-output;
a tube electric current I2 of the following pulse-output from data indicating the relationship between the tube voltage kV2 and a pre-memorized tube voltage and tube electric current;
a variation ΔI between pulse-outputs of said filament electric current based on the present tube electric current I1 of the current pulse-output, the tube electric current I2 of the following pulse-output, the present tube voltage kV1 and the tube voltage kV2 of the following pulse-output; and
calculating a variation C per fixed time interval, between said filament electric current of the current pulse-output and said filament electric current of the following pulse-output, by dividing the variation ΔI by the interval Δt of pulse-output.

11. A method of operating a radiographic examination apparatus, according to claim 10, further comprising the steps of:
providing a filament electric current calculation element in said control element;
said filament electric current calculation element calculating a filament electric current PI of said flash control between pulses; and
whereby the filament electric current calculation element calculates the filament electric current PI of said flash control between pulses according to the following formula PI=G×C/tp+PI2, wherein a gain when changing the filament electric current is G, a flash time between pulses of the flash control between pulses is tp, and the filament electric current of the following pulse-output is PI2.

* * * * *